United States Patent [19]
Atkinson et al.

[11] 4,442,094
[45] Apr. 10, 1984

[54] (3-ARALKYLAMINO-2-OR-PROPOXY)-HETEROCYCLIC COMPOUNDS

[75] Inventors: Joseph G. Atkinson, Montreal, Canada; John J. Baldwin, Gwynedd Valley; David E. McClure, Lansdale, both of Pa.

[73] Assignee: Merck & Co., Inc., Rahway, N.J.

[21] Appl. No.: 350,922

[22] Filed: Feb. 22, 1982

Related U.S. Application Data

[62] Division of Ser. No. 219,726, Dec. 23, 1980, Pat. No. 4,349,673.

[51] Int. Cl.$^3$ .................. C07D 285/24; A61K 31/54
[52] U.S. Cl. ....................................... 424/246; 544/12
[58] Field of Search ...................... 544/12; 424/246

[56] References Cited
U.S. PATENT DOCUMENTS

| | | | |
|---|---|---|---|
| 3,251,837 | 5/1966 | Holland | 544/12 |
| 3,929,793 | 12/1975 | Popelak et al. | 260/268 BC |
| 4,000,282 | 12/1976 | Baldwin | 424/263 |
| 4,081,447 | 3/1978 | Prasad et al. | 260/288 R |
| 4,093,725 | 6/1978 | Roe et al. | 424/250 |
| 4,140,789 | 2/1979 | Jaeggi et al. | 424/248.55 |
| 4,166,851 | 9/1979 | Baldwin et al. | 424/248.55 |

OTHER PUBLICATIONS

Crowther et al., J. Med. Chem. 15, 260 ff, (1972).

*Primary Examiner*—John M. Ford
*Attorney, Agent, or Firm*—Alice O. Robertson; Salvatore C. Mitri; Daniel T. Szura

[57] ABSTRACT

Compounds of the formula Het—O—CH$_2$—CHOR—CH$_2$—NH-aralkyl where Het is a 10 membered N-containing ring are disclosed. The compounds are useful as pharmaceuticals.

14 Claims, No Drawings

(3-ARALKYLAMINO-2-OR-PROPOXY)HETEROCYCLIC COMPOUNDS

This is a division of application Ser. No. 219,726, filed Dec. 23, 1980, now U.S. Pat. No. 4,349,673.

BACKGROUND OF THE INVENTION

The present invention concerns heterocyclic compounds represented by the formula $$\text{Het—O—CH}_2\text{CHOR—CH}_2\text{NH—sub.} \qquad A$$

where sub. is a phenalkyl or phenoxyalkyl type group and their use as pharmaceuticals e.g., for treating glaucoma or hypertension.

Various heterocyclic compounds having an O—CH$_2$—CHOH—CH$_2$—NH—sub. type group are disclosed in the prior art (see, e.g., Crowther et al., J. MED. CHEM. 15, 260 ff (1972), U.S. Pat. No. 4,081,447; U.S. Pat. No. 4,140,789; U.S. Pat. No. 4,166,851; U.S. Pat. No. 4,000,282; U.S. Pat. No. 3,929,793; U.S. Pat. No. 4,093,725).

Novel heterocyclic compounds of Formula A having pharmaceutical activity have been discovered.

SUMMARY OF THE INVENTION

Heterocyclic compounds of the formula Het—OCH$_2$CHOR—CH$_2$—NH—aralkyl where Het is 10-membered N-heterocyclic and their use as pharmaceuticals.

DESCRIPTION OF THE PREFERRED EMBODIMENTS

An embodiment of the present invention is compounds of the formula $$\text{Het—R}_1 \qquad (I)$$

and pharmaceutically acceptable salts thereof wherein Het is (a)

[structure: benzoxazinone-type ring with O, C=O, N-H and fused benzene ring]

or (b)

[structure: benzothiadiazine-type ring with S(=O)$_2$, N, N-H, C$_1$-C$_3$ Alkyl or Hydrogen substituent, fused benzene ring]

wherein
R$_1$ is —OCH$_2$—CHOR$_2$—NHR$_3$
R$_2$ is H or $$\overset{O}{\underset{\|}{C}}-L$$

wherein L is phenyl or C$_1$-C$_5$ alkyl and $$R_3 \text{ is } -\underset{R_5}{\overset{R_4}{\underset{|}{\overset{|}{C}}}}-Y-\!\!\!\!\!\bigcirc\!\!\!\!\!-(R_6)_n$$

wherein
R$_4$ and R$_5$ are independently selected from H and C$_1$-C$_3$ alkyl,
Y is CH$_2$, (CH$_2$)$_2$ or —CH$_2$O—
R$_6$ is H, OH, OCH$_3$, halogen C$_1$-C$_3$alkyl or $$\begin{matrix} -O \\ \phantom{-}\rangle \\ -O \end{matrix}$$

and
n is 1 or 2.

The pharmaceutically acceptable salts are the salts of the Formula I base with suitable organic or inorganic acids. Suitable organic acids include carboxylic acids such as acetic acid, pamoic acid, pivalic acid, oxalic acid, lauric acid, pelargonic acid, citric acid, tartaric acid, maleic acid, oleic acid, propanoic acid, succinic acid, isobutyric acid, malic acid and the like, the noncarboxylic acids such as isethionic acid and methane sulfonic acid. Maleic acid salts are preferred. Suitable inorganic acids are the hydrogen halides e.g. HCl, HI, HBr, phosphoric acid and sulfuric acid. The hydrohalide salts, and especially the hydrochlorides, are preferred. These salts can be prepared by treating the free base with an appropriate amount of a suitable acid, generally in a solvent.

R$_2$ may be H or $$-\overset{\!\!\!\nearrow O}{C}-C_1-C_5\text{alkyl such as } -\overset{\overset{O}{\|}}{C}-CH_3,$$

$$-\overset{\!\!\!\nearrow O}{C}-C(CH_3)_3, \quad -\overset{\!\!\!\nearrow O}{C}-C_5H_{11}$$

and the like. The preferred definition of R$_2$ is H.

R$_3$ is the phenalkyl group $$-\underset{R_5}{\overset{R_4}{\underset{|}{\overset{|}{C}}}}-Y-\!\!\!\!\!\bigcirc\!\!\!\!\!-(R_6)_n$$

Each of R$_4$ and R$_5$ may be C$_1$-C$_3$alkyl e.g. CH$_3$, C$_3$H$_7$, C$_2$H$_5$ and the like or hydrogen. CH$_3$ and H are preferred R$_4$/R$_5$ substituents while it is more preferred when one or both of R$_4$/R$_5$ is CH$_3$. Y is CH$_2$O, CH$_2$ or (CH$_2$)$_2$, with CH$_2$ and (CH$_2$)$_2$ being preferred. R$_6$ is H, OH, OCH$_3$, halogen (Br, Cl, I or F with Br and Cl being preferred), methylenedioxy or C$_1$-C$_3$-alkyl, branched or linear. H and OCH$_3$ are preferred definitions of R$_6$.

Examples illustrating useful R$_6$ groups are

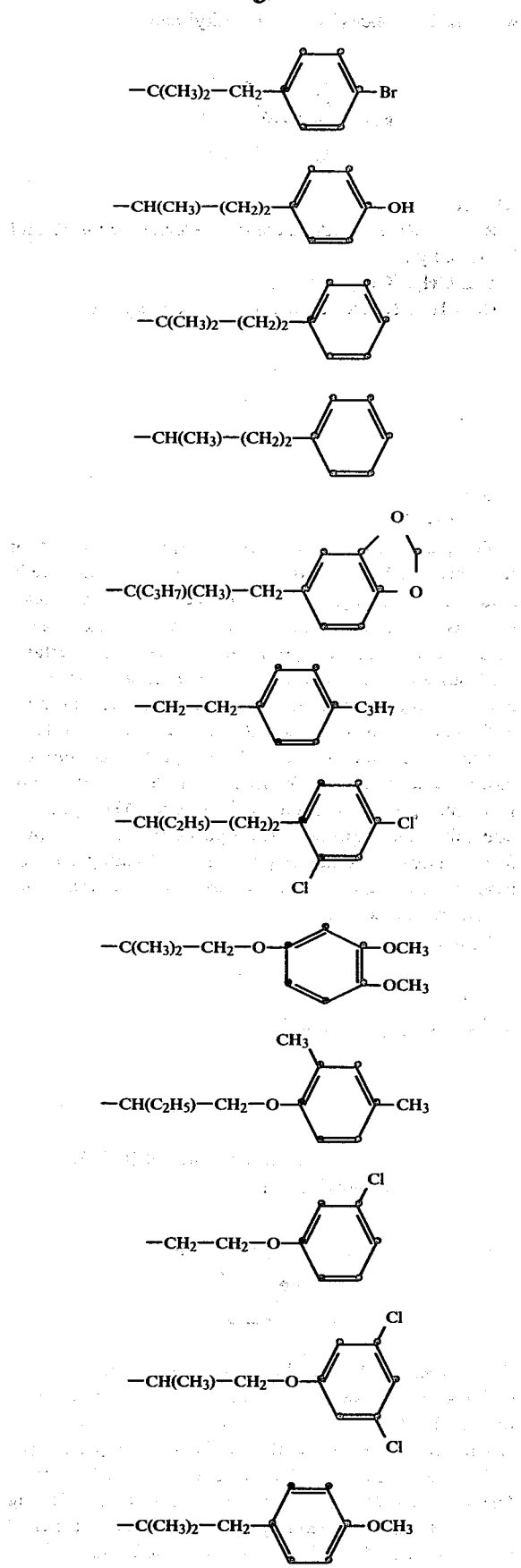

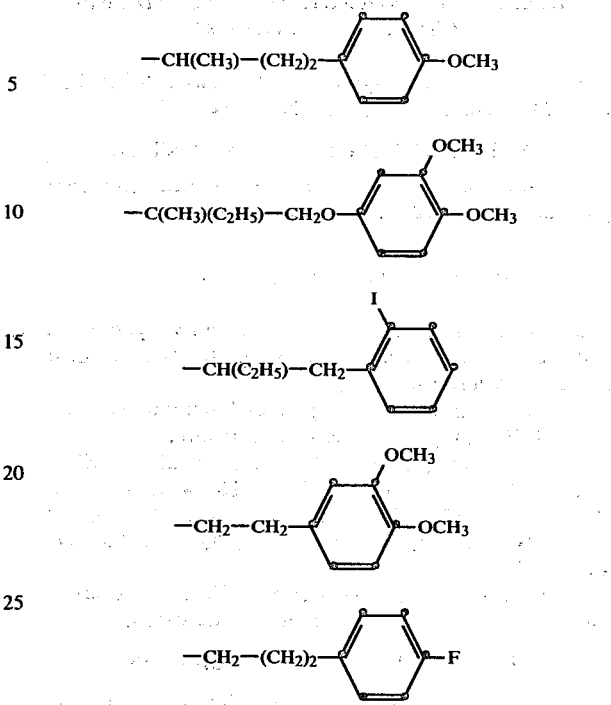

and the like.

The compounds of formula I have one chiral center at the 2-position in the propoxy substituent and can have a second chiral center when the $R_4$ and $R_5$ substituents in the $R_3$ group are different. The chiral centers confer optical activity on the formula I compounds.

All the optical isomer forms, that is mixtures of enantiomers or diastereomers, e.g. racemates as well as individual enantiomers or diasteriomers of formula I are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

A compound of Formula I is useful for treating glaucoma since it decreases intraocular pressure when topically administered to the eye. The ability to lower intraocular pressure is determined using an in-vivo protocol in a rabbit model.

Said compound is preferably administered in the form of an opthalmic pharmaceutical composition adapted for topical administration to the eye such as a solution, an ointment or as a solid insert. Formulations of the compound may contain from 0.01 to 5% and especially 0.5 to 2% of medicament. Higher dosages as, for example, about 10% or lower dosages can be employed provided the dose is effective in lowering intraocular pressure. As a unit dosage form between 0.001 to 5.0 mg., preferably 0.005 to 2.0 mg., and especially 0.005 to 1.0 mg. of the compound is generally applied to the human eye.

The pharmaceutical composition which contains the compound may be conveniently admixed with a non-toxic pharmaceutical inorganic carrier. Typical of pharmaceutically acceptable carriers are, for example, water; mixtures of water and other water miscible solvents such as lower alkanols or aralkanols; vegetable oils; polyalkylene glycols; petroleum based jelly; ethyl cellulose; ethyl oleate; carboxymethylcellulose; polyvinylpyrrolidone; isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000 bacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetate, glyconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts; natural products such as gelatin, alginates, pectins, tragacanth, karaya, chondrus, agar, acacid; the starch derivatives such as starch acetate, hydroxyethyl starch ethers, hydroxypropyl starch, as well as other synthetic derivatives such as poly vinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert is available in several polymeric forms, all of which are suitable in the preparation of these inserts. Thus, the product sold by Hercules, Inc. of Wilmington, De. under the name KLUCEL such as KLUCEL HF, HWF, MF, GF, JF, LF and EF which are intended for fool or pharmaceutical use are particularly useful. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX, a polymer supplied by Union Carbide Co., may be used having a molecular weight of about 50,000 to 5,000,000 or more and preferably 3,000,000 to 4,000,000. Other specific about 1,000,000 or more, preferably up to about 350,000 and especially about 20,000 to 60,000; polyvinyl alcohol having a molecular weight of from about 30,000 to 1,000,000 or more particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941. It is clear that for the purpose of this invention the type and molecular weight of the polymer is not critical. Any water soluble polymers can be used having an average molecular weight which will afford dissolution of the polymer and accordingly the medicament in any desired length of time. The inserts, therefore, can be prepared to allow for retention and accordingly effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford insects of suitable size for administration in the eye.

The insert can be of any suitable size to readily fit into the eye. For example, castings or compression molded films having a thickness of about 0.25 mm. to 15.0 mm. can be subdivided to obtain suitable inserts. Rectangular segments of the cast or compressed film having a thickness between about 0.5 and 1.5 mm can be cut to afford shapes such as rectangular plates of 4×5-20 mm. or ovals of comparable size. Similarly, extruded rods having a diameter between about 0.5 and 1.5 mm. can be cut into suitable sections to provide the desired amount of polymer. For example, rods of 1.0 to 1.5 mm. in diameter and about 20 mm. long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7-8; usually up to about 2% by weight of polymer. The insert may contain from about 1 mg. to 100 mg. of water soluble polymer, more particularly from .5 to 5 mg. and especially from 5 to 20 mg. The medicament is present from about 0.1 to about 25% by weight of insert.

The ability of the Formula I compound to lower intraocular pressure is determined in rabbits with experimental glaucoma induced by intraocular injection of α-chymotrypsin. Compounds of Formula I are effective in lowering intraocular pressure after topical application. Pressure is reduced in the normal and the glaucomatous eye.

The compounds (Formula I) of the present invention have β-adrenergic blocking activity. This β-adrenergic blocking activity is determined by measuring the ability of representative compounds to block the β-adrenergic stimulant effect of isoproterenol in a test animal.

The compounds of the present invention also have α-adrenergic blocking activity. This α-adrenergic blocking activity is determined, (a) in vitro by measuring the ability of a representative Formula I compound to displace radio labeled α-adrenergic antagonist from a tissue substrate or (b) in vivo, by measuring the ability of representative Formula I compound to block the α-adrenergic stimulant effect of phenylephrine in anesthetized mormotensive animals.

The present compounds exhibit antihypertensive activity of immediate onset. This rapid onset antihypertensive activity is determined by administering a representative compound of the present invention to spontaneously hypertensive (SH) rats and measuring the effect on blood pressure.

The α- and β-adrenergic blocking activity of the present compounds indicates that the compounds may be useful in humans for treating cardiovascular conditions susceptible to β-blockade therapy (e.g., angina pectoris, arrhythmia) while minimizing bronchoconstriction via α-adrenergic blockage. This dual α/β-blocking effect may be useful in treating hypertension caused by pheochromocytoma.

For use as α/β-adrenergic blocking agents, and/or antihypertensive agents the compounds of the present invention can be administered orally, by inhalation, by suppository or parenterally, i.e., intravenously, intraperitoneally, etc. and in any suitable dosage form. The compounds may be offered in a form (1) for oral administration, e.g., as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material, or (2) for parenteral administration, dissolved, dispersed, or emulsified in a suitable liquid carrier or diluent or (3) as an aerosol or (4) as a suppository. The ratio of active ingredient (present compound) to compounding ingredients will vary as the dosage form required. Conventional procedures are used to prepare the pharmaceutical formulations.

The effective daily dosage level for α/β blocker based utilities for the present compounds may be varied from about 10 mg. to about 3000 mg. Daily doses ranging from about 100 to about 2500 mg. are preferred, with about 200 to about 1000 mg. being a more preferred range. Oral administration is preferred. Either single or multiple daily doses may be administered depending on unit dosage.

Compounds of formula I also have bronchodilator activity. This is determined by measuring the effectiveness of the compound to antagonize slow reacting substances of anaphylaxis (SRS-A). The compounds are thus useful to treat conditions in mammals especially human beings which benefit from bronchodilatation such as asthma, etc. For use as a bronchodilator, the compound is administered orally or parenterally in conventional dosage form such as tablet, capsule, solution, dispersion, emulsion and the like. The compound may also be administered as a spray or an aerosol using an appropriate delivery device and formulation. The oral route is preferred.

Sufficient formula I compound is administered to produce the desired level of bronchodilation. Daily dosages for oral or parenteral administration may range from about 1 mg to about 300 mg, and preferably from about 2 to about 150 mg. Spray or aerosol delivery will be in metered doses ranging from about 50 to about 1000 mcg, administered as needed.

Thus, other embodiments of the present invention are the pharmaceutical compositions containing a therapeutically effective amount of the Formula I compound and methods for treating hypertension, other cardiovascular conditions, or glaucoma; for lowering intraocular pressure; or treating asthma and the like.

The compounds of the present invention can be prepared by any convenient process.

A convenient process for preparing the present compound is by treating an appropriate substituted epoxide with a suitable amine as illustrated by the following reaction equation:

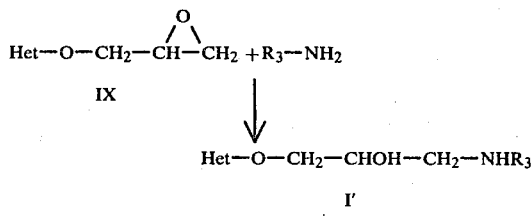

This reaction is conveniently carried out with a slight excess of the amine (R₃NH₂) reactant in a lower alkanol such as methanol, ethanol, isopropanol, etc., as a solvent. Temperatures from 25° C. up to the boiling of the solvent may be used, with a range of 65° to 90° C. being preferred.

The product from the epoxide/R₃NH₂ reaction is ordinarily a racemate, and can be separated using conventional resolution procedures.

If a single optical isomer of the formula IX epoxide is used, as the reactant, the product obtained is the corresponding single optical isomer e.g., (S)-IX+R₃NH₂→(S)-I'.

The optically active epoxide intermediates of formula IX can be prepared according to the reaction illustrated below.

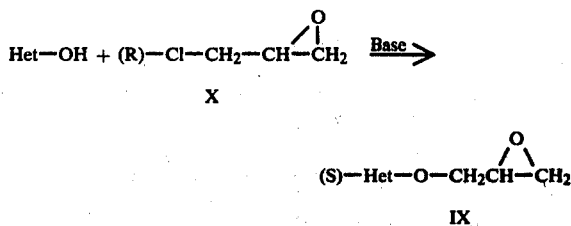

Conventional reaction conditions are used. Conversely, if the (S) isomer of formula X is used, the corresponding (R) isomer of formula IX is obtained. Preparation of the intermediates will be shown in the examples below.

Compounds of the present invention wherein R₂ is other than hydrogen are conveniently prepared by treating the corresponding heterocycle where R₂ is hydrogen with an appropriate acylating agent such as an acyl halide, e.g., undecanoyl chloride, pivaloyl chloride, benzoylchloride, p-methoxybenzoyl chloride or an anhydride, e.g. acetic anhydride, and the like. The reaction is illustrated by the following equation:

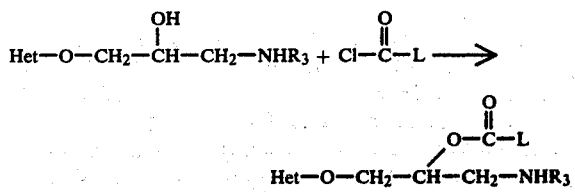

The following examples illustrate preparation of representative compounds of formula I. Temperatures are in degrees Celsius.

EXAMPLE 1

Preparation 1-[(1,1-Dioxo-3-methyl-4H-1,2,4-benzothiadiazine-7-yl)oxy]-3-[1-methyl-3-phenylpropyl)amino]-2-propanol.HCl (C) of the formula

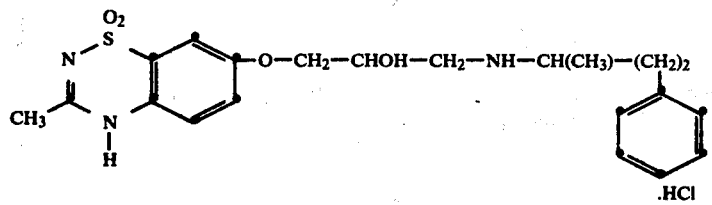

(A) 7-Hydroxy-3-methyl-4H—1,2,4-benzothiadiazine-1,1-dioxide (A)

Pyridine.HCl (20 g) is heated to 210° C. and 5 g of 7-methoxy-3-methyl-4H-1,2,4-benzothiadiazine-1,1-dioxide are added. This mixture was kept at about 210° C. for about 1½ hours. The mixture was then cooled slightly and about 60 ml of ice cold water was added with stirring. This mixture was filtered and the solid washed with 25 ml. of cold water and dried yielding 3.5 g of 7-hydroxy-3-methyl-4H-1,2,4-benzothiadiazine-1,1-dioxide (A). An additional 0.63 g of A was recovered from the filtrate to allowing it to stand in the refrigerator for about one hour. Total yield of this product was 4.13 g (88%), m.p. 333°-336° C. (dec.).

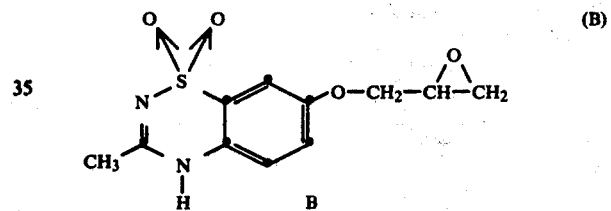

To a solution of A (10 g) and CH₃ONa (6.0 g) in 200 ml of absolute ethanol was added 45 ml. of epichlorohydrin and the mixture was reluxed for about 20 minutes. The reaction mixture was then decolorized directly with carbon black, and filtered through Celite. The filtrate was evaporated to dryness and the residue obtained was chromatographed (600 g. silica gel—E. Merck) using 10% MeOH/90% CH₂Cl₂ as the eluant. Fractions 5 to 9 contained 3.55 gm. of pure B were obtained (total yield 57%).

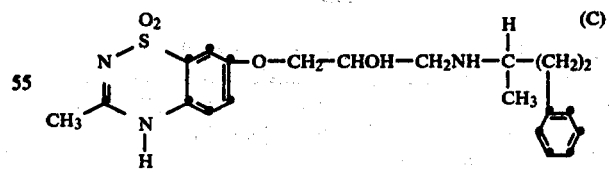

Compound B (1.8 g) and 1.05 g of 1-methyl-3-phenyl propylamine was dissolved in about 25 ml of absolute ethanol. This solution was refluxed for about 4 hours (TLC indicated reaction was complete). The solution was then evaporated to dryness and the resultant residue was treated with ether and decanted. The residue was chromatographed (100 g silica gel—E. Merck) and eluted with 20% MeOH/80% CH₂Cl₂ to yield 1.6 g of product C.

The product C was converted to its HCl salt (m.p. 197°-202°) by treating C with conc. HCl in ethanol recrystallizing the product and drying it at 105° C.

When

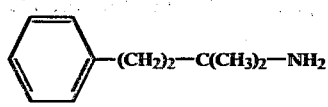

was substituted for 1-methyl-3-phenylpropylamine in Example 1 the analog of C where R₃ is

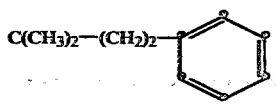

was obtained.

When an amine of the formula

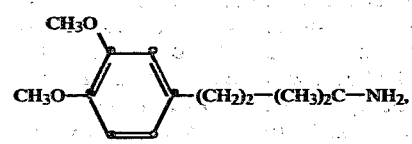

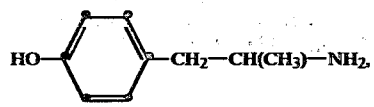

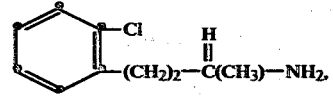

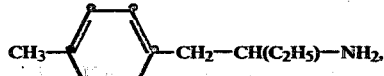

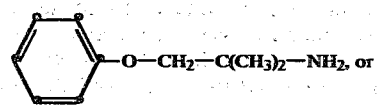

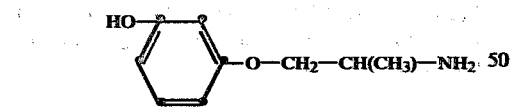

and the like is used in place of the 1-methyl-3-phenyl-propylamine in Example 1, analogous N-substituted compounds are obtained. Where the phenyl group bears an OH substituent, the OH may require protection e.g. with an acyl group such as $CH_3-C\overset{O}{\underset{}{\parallel}}-$ or subsequent deprotection as a final step in the synthesis.

By substituting a heterocyclic compound of the following listed formulae, for the 7-hydroxy-3-methyl-4H-1,2,4-benzothiadiazine-1,1-dioxide in Example 1, the corresponding heterocyclic analog of the Example 1 product is obtained:

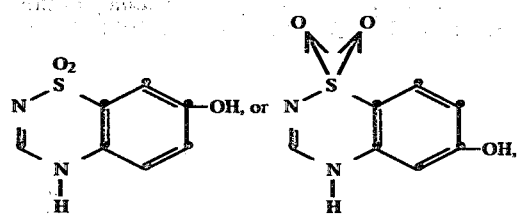

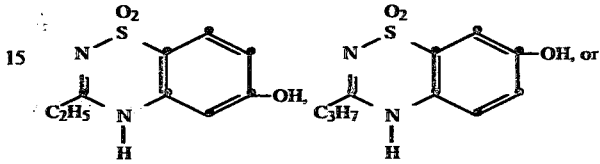

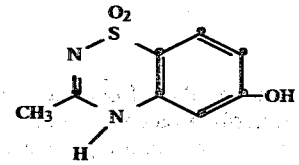

EXAMPLE 2

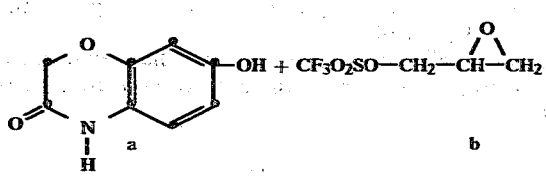

In a reaction similar to Example 1, the epoxide 1 was prepared using KH to generate the potassium salt of the phenol a in THF and then reacting this salt with the oxirane b in refluxing THF. The crude epoxide 1 was treated with 1 molar equivalent of 1-methyl-3-phenyl-propylamine at 115° C. overnight to yield the product 2. This product 2 was purified by conventional chromatography. Final purification was accomplished by conversion to the fumarate salt in isopropanol and recovering pure 2 hemihydrate from the fumarate salt. Elemental analysis of 2 hemihydrate gave Calculated: C=60.53%, N=5.04%, H=7.07%. Actual: C=60.34%, N=4.82%, H=6.57%.

Claims to the invention follow.

What is claimed is:

1. A compound of the formula:

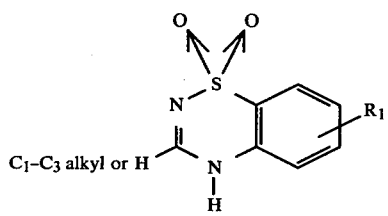

individual isomers and pharmaceutically acceptable salts thereof wherein $R_1$ is —OCH$_2$—CHOR$_2$—CH$_2$—NHR$_3$ $R_2$ is H or

wherein

L is phenyl or $C_1$–$C_5$ alkyl and

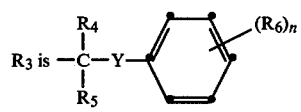

wherein $R_4$ and $R_5$ are independently selected from H and $C_1$–$C_3$alkyl,

Y is CH$_2$, (CH$_2$)$_2$ or —CH$_2$O—

$R_6$ is H, OH, OCH$_3$, halogen, $C_1$–$C_3$alkyl or

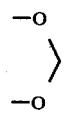

and n is 1 or 2.

2. The compound of claim 1 wherein $R_2$ is H.

3. The compound of claim 2 wherein $R_6$ is H, OH or OCH$_3$.

4. The compound of claim 3 wherein Y is CH$_2$O.

5. The compound of claim 3 wherein Y is CH$_2$ or (CH$_2$)$_2$.

6. The compound of claim 5 wherein Y is (CH$_2$)$_2$.

7. The compound of claim 5 where $R_4$ and $R_5$ are CH$_3$ or H.

8. The compound of claim 7 wherein $R_6$ is H or OCH$_3$.

9. The compound of claim 8 wherein $R_3$ is

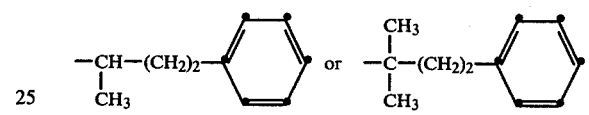

10. Compound of claim 1 having the formula

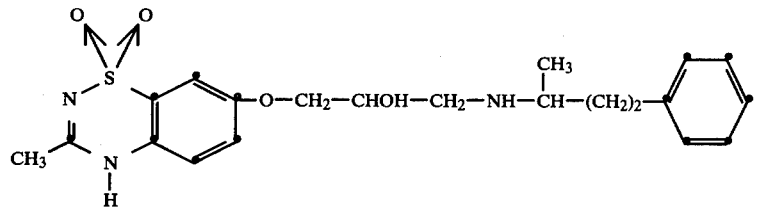

or

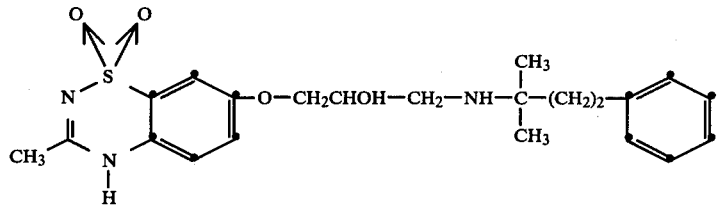

11. The individual isomers of the claim 10 compounds.

12. The racemates of the claim 10 compounds.

13. A pharmaceutical composition for reducing intraocular pressure comprising a pharmaceutical carrier; and, an intraocular pressure reductive amount of a compound of claim 1.

14. A method for reducing intraocular pressure in a patent in need of such treatment which comprises administering to such patient an intraocular pressure reductive amount of a compound of claim 1.

* * * * *